Figure 1:
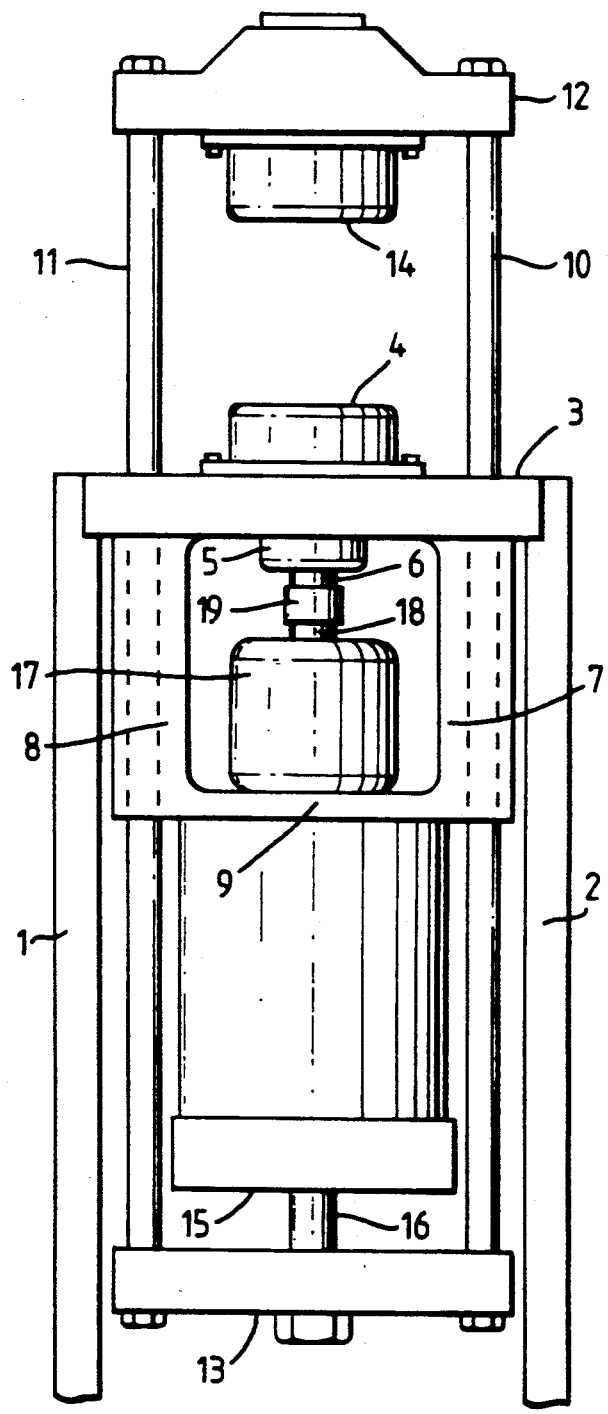

United States Patent [19]
Burhin et al.

[11] Patent Number: 5,079,956
[45] Date of Patent: Jan. 14, 1992

[54] TESTING OF VISCOELASTIC MATERIALS

[75] Inventors: Henri A. G. Burhin, Beauvechain, Belgium; David P. J. King, Lechlade, England; Willy A. G. Spreutels, Sandton, South Africa

[73] Assignee: Monsanto Europe, S.A., Brussels, Belgium

[21] Appl. No.: 583,736

[22] Filed: Sep. 17, 1990

[51] Int. Cl.$^5$ ............................................... G01N 3/24
[52] U.S. Cl. ........................................ 73/846; 73/60; 374/47
[58] Field of Search ............... 73/846, 843, 841, 60, 73/59; 374/47, 48

[56] References Cited

U.S. PATENT DOCUMENTS

| | | |
|---|---|---|
| 2,037,529 | 4/1936 | Mooney ................... 265/11 |
| 3,479,858 | 11/1969 | Umeno et al. |
| 3,488,992 | 1/1970 | Veith et al. |
| 4,343,190 | 8/1982 | Danko et al. .............. 73/846 |
| 4,552,025 | 11/1985 | Barker et al. ............. 73/846 |

FOREIGN PATENT DOCUMENTS

| | | |
|---|---|---|
| 1036904 | 4/1963 | United Kingdom. |
| 1196868 | 7/1970 | United Kingdom ......... 73/60 |

Primary Examiner—Tom Noland
Assistant Examiner—Joseph W. Roskos
Attorney, Agent, or Firm—Gordon B. Seward

[57] ABSTRACT

In a method of testing a sample of viscoelastic material held under pressure between two opposing, temperature-controlled dies, the sample is subjected to an oscillatory, rotary shearing force which has a predetermined amplitude and a frequency within the range 0.001 to 2 Hz, and a torque which is indicative of the response of the sample to the shearing force is measured, at least one measurement of the torque being made when the predetermined amplitude is at least ±10° but not greater than ±360°.

13 Claims, 8 Drawing Sheets

PHASE IN DEGREES

PHASE IN DEGREES

PHASE IN DEGREES

DIE ANGLE 20 DEG.

PHASE IN DEGREES

DIE ANGLE 50 DEG.

TESTING OF VISCOELASTIC MATERIALS

This invention relates to a method and apparatus for measuring the properties of viscoelastic materials.

The relevant prior art includes the plastometer of Mooney described in U.S. Pat. No. 2,037,529, and the rheometer described in U.S. Pat. No. 1,036,904. In each of these instruments, a sample of the material to be tested is enclosed in a cavity formed between two opposing dies, rotational shear is applied to the sample by means of a rotor embedded in the sample, and the torque required to apply the shear is measured. In the former instrument, the rotation of the rotor is continuous; in the latter the rotation is oscillatory.

Other instruments in which an oscillatory, rotary shearing force is applied to a sample of viscoelastic material held between two opposing dies are those described in U.S. Pat. No. 3,479,858, U.S. Pat. No. 3,488,992, U.S. Pat. No. 4,343,190, and U.S. Pat. No. 4,552,025. In these instruments, the force is applied by rotation of one die relative to the other, and the measurements made are of the torque required to apply the shearing force or of the torque induced in the second die (reaction torque) when the first (driven) die is rotated.

For the operation of prior art instruments involving an oscillatory shearing force, relatively small angles of oscillation are envisaged. This is because such instruments have been primarily intended to obtain information about the behaviour of compounded rubber stocks immediately prior to and during vulcanisation. For example, U.S. Pat. No. 1,036,904 mentions oscillation through a small angle, for example 2°; U.S. Pat. No. 3,479,858 refers to reciprocal rotation through a given angle (usually not more than 15°); and U.S. Pat. No. 4,343,190 and U.S. Pat. No. 4,552,025 state that the rotation is preferably sinusoidal and is preferably performed through an angle of from 0.1° to 10°.

As regards the frequency of oscillation in the prior art methods, U.S. Pat. No. 3,681,980 mentions frequencies of up to 3,600 cycles per minute (60 Hz), with an example at 852 cycles per minute (14.2 Hz), and U.S. Pat. No. 4,343,190 and U.S. Pat. No. 4,552,025 mention frequencies of from 1 to 2000 cycles per minute (0.0167 to 33.33 Hz) and from 1 to 10000 cycles per minute (0.0167 to 166.67 Hz) respectively.

A characteristic of the method of testing disclosed in U.S. Pat. No. 4,552,025 is that a sample of viscoelastic material is held at a predetermined temperature while the force induced in reaction to the deflection of the material at two or more oscillatory frequencies is measured. The sample is then held at another, higher, predetermined temperature while the said force is measured at one or more oscillatory frequencies. The method is intended primarily to give information, derivable from the measurements at the first predetermined temperature, about the rheological behaviour of rubber compounds at typical prevulcanization temperatures, and information about the curing characteristics of the same compound during vulcanisation at the second, higher temperature.

We have now found that data derivable by testing samples of viscoelastic materials which do not thermoset during the period of the test are much more discriminating in distinguishing different materials or in identifying deviations from a standard if the sample is subjected to a rotatory, oscillatory shearing force having a greater amplitude of oscillation than any disclosed or suggested by the prior art. Oscillation frequencies towards the lower end of the ranges mentioned in the above prior art documents or below are employed.

The method of the invention is a method of testing a sample of viscoelastic material held under pressure between two opposing, temperature-controlled dies, which comprises subjecting the sample to an oscillatory, rotary shearing force having a predetermined amplitude and frequency, and measuring a torque which is indicative of the response of the sample to the shearing force, characterised in that at least one measurement of said torque is made when the said predetermined amplitude is at least ±10°, but not greater than ±360°, and said frequency is within the range 0.001 to 2 Hz.

The apparatus of the invention comprises two opposing dies movable between an open position and a closed position, and adapted, when in the closed position, to contain between them a sample of viscoelastic material under pressure, means for controlling the temperature of the dies, means for applying an oscillatory, rotary shearing force to a sample of viscoelastic material contained between the closed dies, and means for measuring a torque which is indicative of the response of the sample to the shearing force, characterised in that the means for applying the shearing force comprise means for applying the shearing force at at least one amplitude of oscillation within the range ±10° to ±360° and a frequency of oscillation within the range 0.001 to 2 Hz.

In preferred embodiments of the method and apparatus, the shearing force is applied to the sample by oscillatory rotation of one of the dies with respect to the other, and the torque indicative of the response of the sample to the shearing force is the reaction torque measured on the other die. Other arrangements are possible, however. For example, the force could be applied to the sample by means of a rotor embedded in the sample as in the Mooney viscometer or the rheometer described in 1,036,904; and the torque which is measured to indicate the response of the sample to the oscillatory shearing force could be the torque applied to the said one of the dies or to the rotor.

Preferably, the said at least one amplitude of oscillation is an amplitude within the range ±10 to ±200°, and more preferably within the range ±20° to ±120°. Depending on the viscoelastic material to be tested and the data which it is desired to derive from the test, torque measurements may be made at a single amplitude of oscillation or at a series of two or more different amplitudes. In the case of measurements at single amplitude, this is preferably an amplitude within the range ±20° to ±120°, for example within the range ±40° to ±120°. In the case of measurements at a series of different amplitudes, the selected amplitudes preferably include two or more within the range ±10° to ±120°, but the series can also include measurements at smaller amplitudes, for example ±5°, or larger amplitudes. Moreover, measurements at a given amplitude can be made at a single frequency or at a number of different frequencies of oscillation; and measurements at a series of amplitudes can be made at a fixed temperature throughout, or one or more measurements can be made at one temperature and one or more at a different temperature.

The oscillatory rotation in the method and apparatus of the invention is preferably sinusoidal. Useful parameters for characterising viscoelastic materials derivable from torque measurements under such conditions are the elastic or storage modulus S', the viscous or loss modulus S" and the tangent of the loss angle (delta) which is the ratio S"/S'. S' can be calculated from the torque measured at the point of maximum displacement, while S" can be calculated from the torque at zero displacement. However, measurement of the torque at a series of sampling points throughout the oscillation can provide useful data about the sample. For example, the method of the present invention can incorporate the features of the method of U.S. Pat. No. 4,794,788 which comprises (A) separately subjecting both a sample of the material and a standard to a sinusoidal shearing force, (B) separately measuring a material response and a standard response at at least three displacement data points equally spaced throughout a cycle of oscillation (C) separately applying a calculation operation to the data points to (i) convert the material data points into values representing either a storage modulus or a loss modulus of the material; and to (ii) convert the standard data points into values representing a standard torque and a standard phase angle, and (D) correcting the values representing the storage modulus or loss modulus for the material. As explained in U.S. Pat. No. 4,794,788, the optimum number of data points is 16 per cycle.

In certain instances an improved characterisation of the viscoelastic material can be achieved by subjecting the torque response to harmonic analysis. The response of the viscoelastic material at large angle deformation produces a non-sinusoidal torque envelope. The shape of the torque curve can be fully described mathematically by using Fourier transformations by means of which all the dominant sine wave frequencies and amplitudes can be determined.

Any or all of the parameters to be used for characterising the viscoelastic elastic material can be electronically derived from the torque measurements during the course of the test and continuously displayed.

In the preferred form of die, the opposing faces are shallow, coaxial cones disposed so that the separation of the faces increases with the radial distance from the axis. A preferred arrangement is for the lower die face to have the form of a cone and for the upper die face to be an inverted cone, the use of flat-topped cones being particularly preferred. The die faces will normally be provided with radial grooves or similar means to prevent slippage of a sample of viscoelastic material held in the die.

In preferred embodiments of the apparatus, the lower die is driven from a computer-controlled electric motor located beneath the die and having its output shaft coaxial with and rigidly coupled to the die. The computer is programmed so that the output shaft of the motor moves at the desired angular displacement and frequency or through a sequence of desired angular displacements and frequencies. Although a sinusoidal oscillation is often preferred, the arrangement described above allows the rotary oscillation of the lower die in other modes. For example, by suitable electronic processing of torque measurements in a particular embodiment of the invention using constant oscillating speed, it is possible to derive information concerning the rheological properties of viscoelastic materials which corresponds essentially to that provided by the Mooney viscometer.

Such a method and apparatus in fact represent an improvement over the current Mooney method because the latter suffers from drift in torque measurements which is the result of the continuous rotation of the rotor.

The form of oscillatory motion is not limited, and can be, for example, sinusoidal, constant angular velocity, ramp, triangular or any combination of different motions.

FIG. 1 of the drawings shows diagrammatically certain elements of an apparatus embodying the invention.

Figure 2:
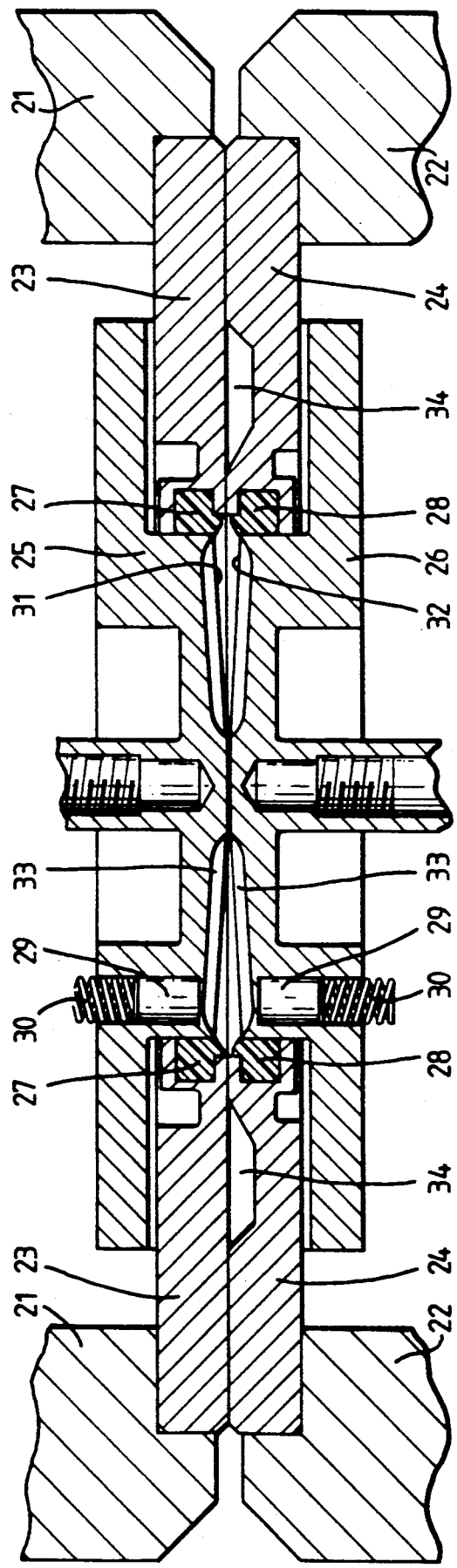
Figure 3:
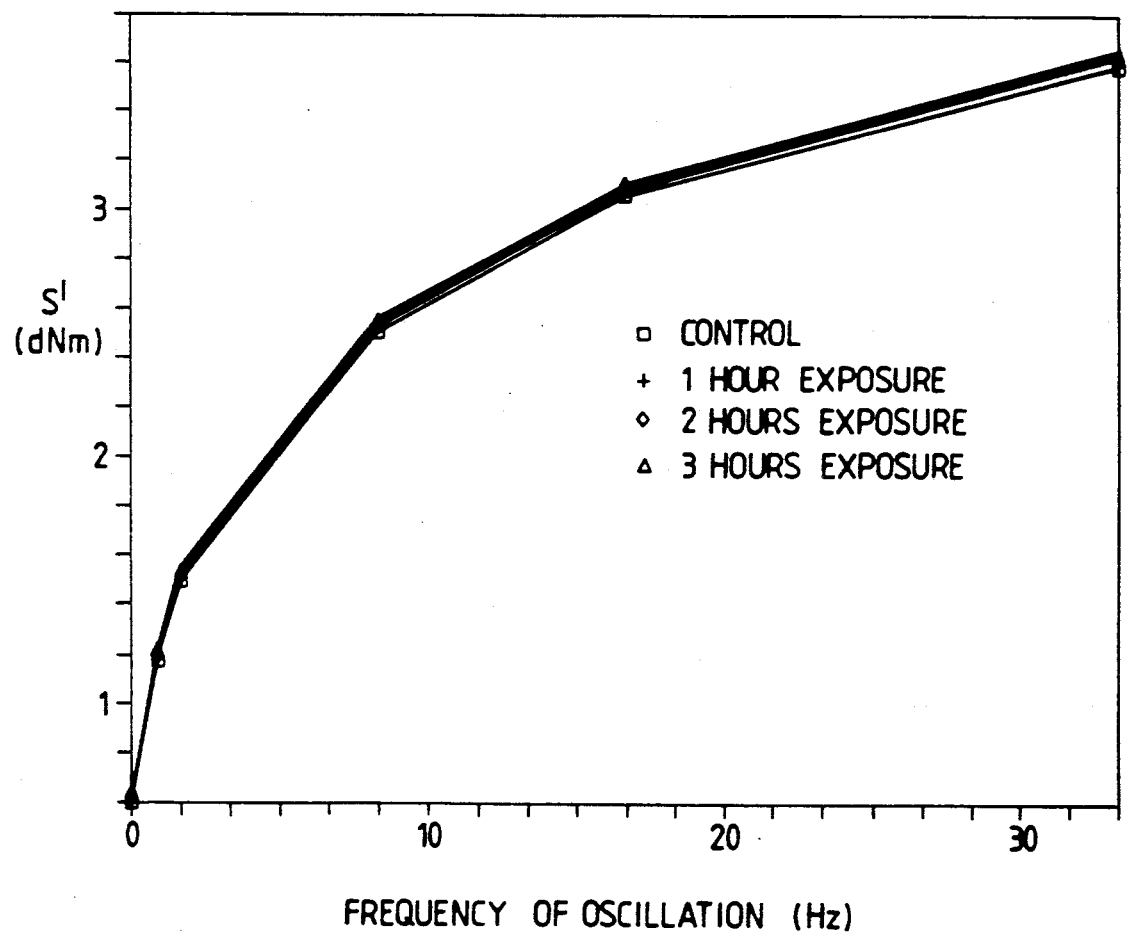

FIG. 2 of the drawings is a vertical cross-section showing dies in the closed position. FIGS. 4 to 8 represent graphically results obtained by the method of the invention, while FIG. 3 represents results obtained by a prior art method.

Referring to FIG. 1 of the drawings, the members (1), (2) and (3) are respectively left and right vertical, and horizontal components of an outer frame which is supported on a base (not shown). A lower die assembly comprising a die housing (4) and a housing (5) for a drive shaft (6) connected at its upper end to a lower die (not shown), is mounted in the horizontal member (3). An inner frame, which is located beneath the horizontal member (3), has vertical portions (7) and (8) and a lower horizontal portion (9). Tie rods (10) and (11) which pass through the horizontal member (3) are attached at their upper ends to an upper crosshead (12) and at their lower ends to a lower crosshead (13). An upper die assembly comprising an upper die housing (14) is mounted in the upper crosshead.

A pneumatic cylinder (15) mounted beneath the horizontal portion (9) of the inner frame has a cylinder rod (16) which is connected to the lower crosshead (13). Actuation of the pneumatic cylinder causes the assembly consisting of the cylinder rod (16), lower crosshead (13) tie rods (10) and (11) and upper crosshead (12) to travel downwards, thus bringing the upper die housing (14), the lower die housing (4) and the dies into the closed position shown in FIG. 2.

The drive system to the lower die comprises a computer-controlled electric motor (17), for example a Compumotor stepper motor with 25,000 steps per revolution, mounted with its output shaft (18) coaxial with the drive shaft (6) to the lower die, the two shafts being coupled by means of a sleeve (19).

In FIG. 2 of the drawings, there are illustrated parts of upper and lower die assemblies. The lower edge of the upper die housing and the upper edge of the lower die housing are indicated at (21) and (22) respectively. Other parts shown are sealing plates (23) and (24), which are attached to the edges of the die housings, upper and lower dies plates, (25) and (26) respectively, and sealing rings (27) and (28). Each die plate has a cylindrical cavity (29) adapted to accommodate a temperature probe (30). The opposing faces (31) and (32) of the die plates which define the die cavity are in the form of shallow flat-topped cones having radial grooves (33). Thus a sample in the die cavity has a thin, flat circular portion in the middle and an outer portion which increases in thickness radially outwards. The function of &he channel (34) in the lower sealing plate (24) is to accommodate any overflow of the sample material which is expressed during closure of the dies.

Parts of the upper and lower die assemblies which are not illustrated, being generally similar to those shown in FIG. 2 of U.S. Pat. No. 4,552,025 are (in the upper assembly) a torque transducer, means connecting the upper die to the force transducer, and heating elements; and in the lower die assembly, a shaft coaxial with the lower die, means connecting the die to the shaft, a bearing housing for the shaft, and heating elements for the die.

Figure 4:
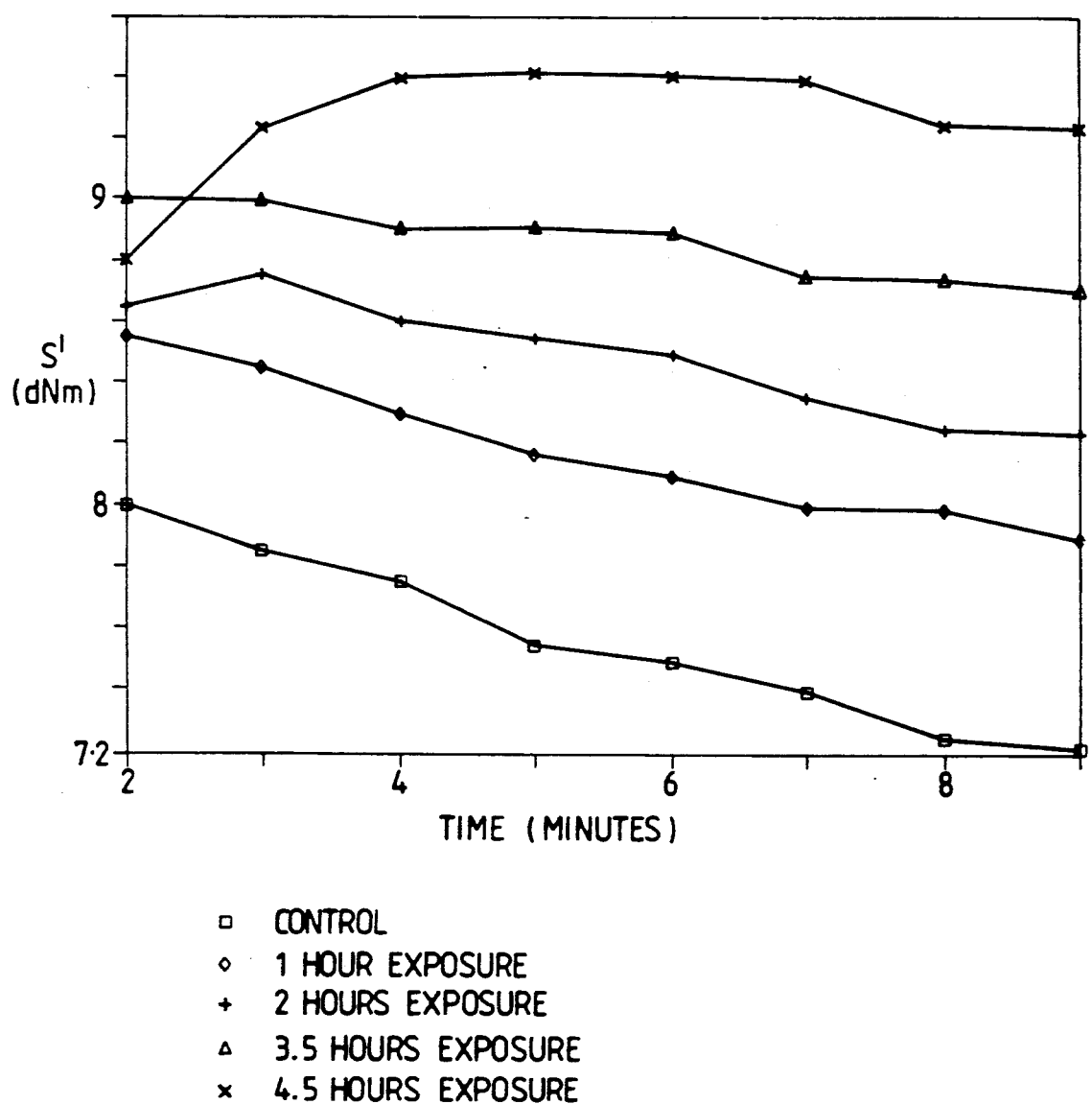
Figure 5:
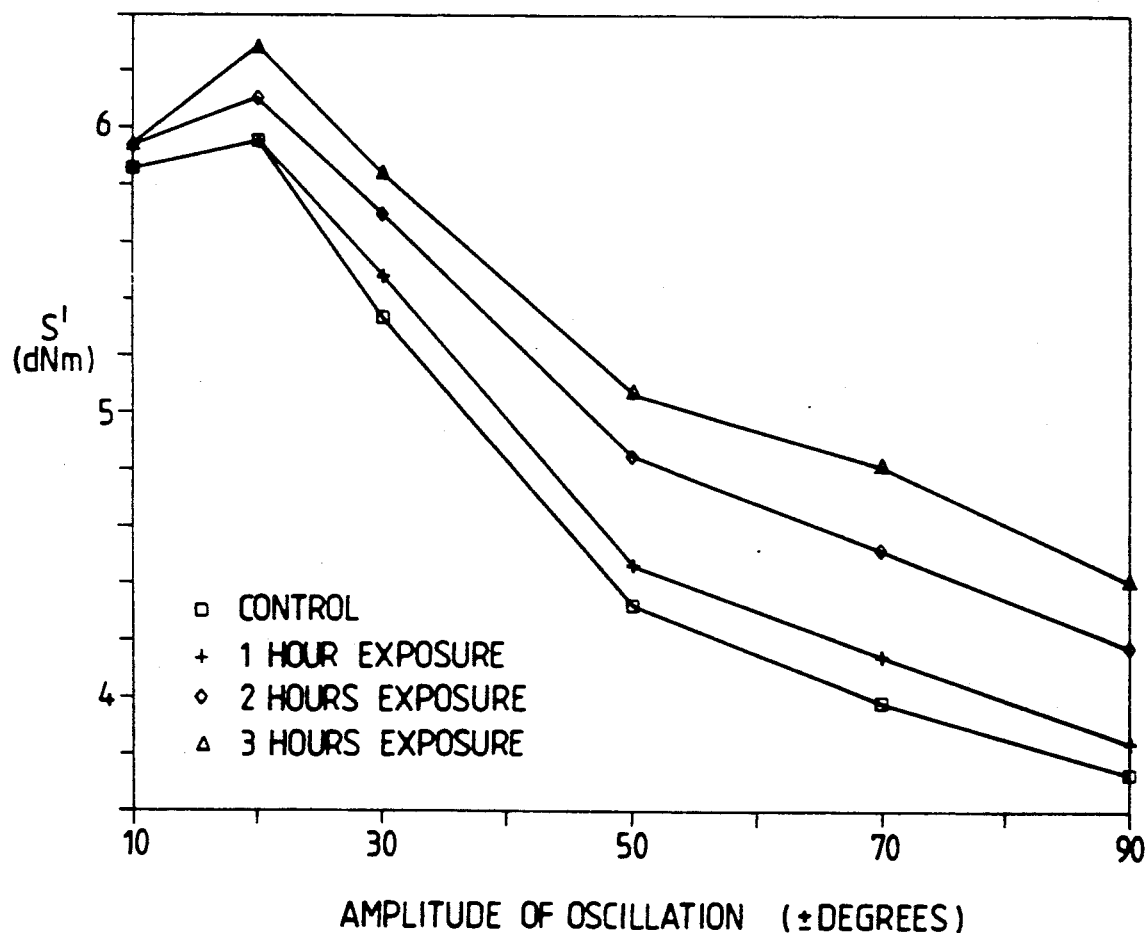
Figure 6:
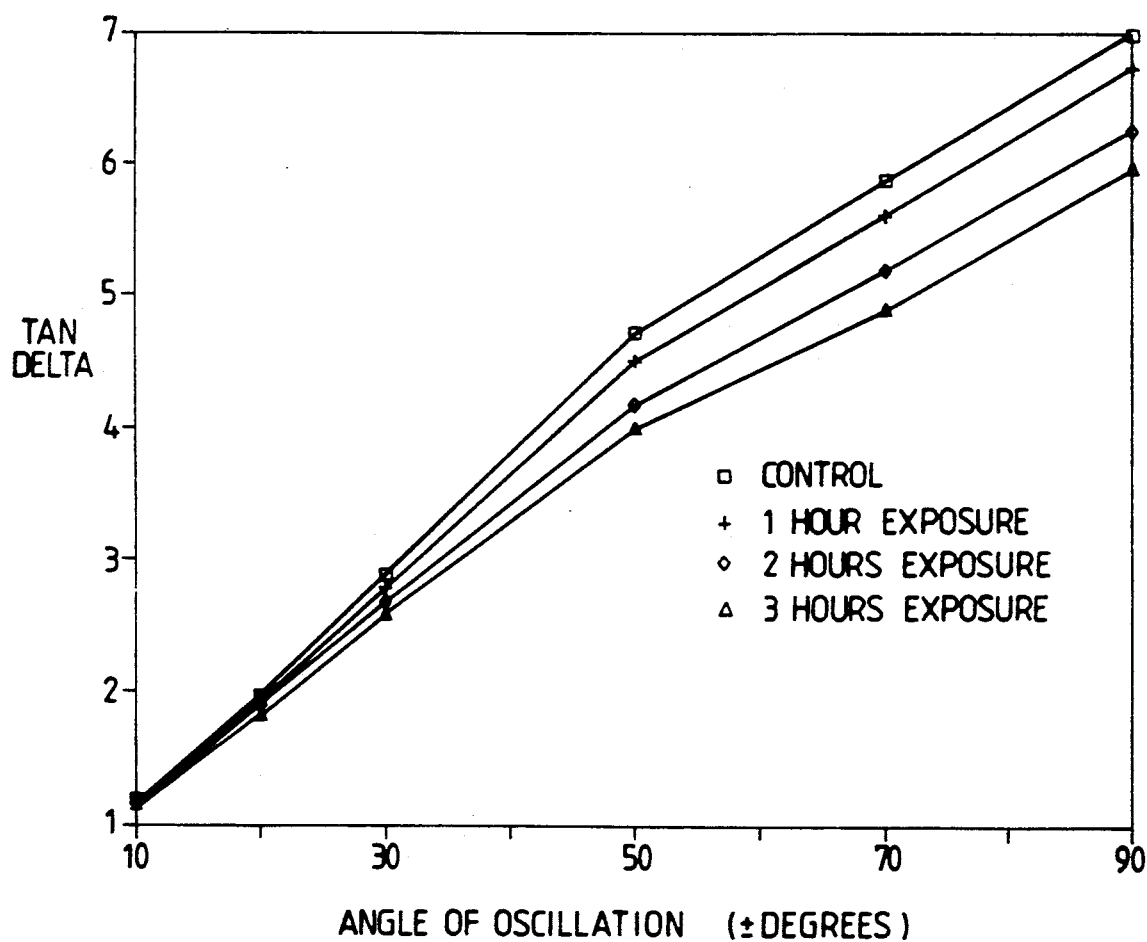

FIGS. 3, 4, 5 and 6 present graphically results obtained in tests on styrene-butadiene rubber SBR 1502 after exposing the rubber for various periods to U.V. radiation, thereby inducing gel formation in the rubber. The results illustrated in FIG. 3 were obtained by employing the procedure of the first step of the method of U.S. Pat. No. 4,552,025, namely by holding a sample of the rubber at a fixed temperature (100° C.) while measuring the reaction torque at a number of different oscillatory frequencies. It will be seen that the plots of frequency against S' are not sufficiently separated to distinguish a non-irradiated sample (control) nor the samples of rubber which has been exposed to various periods of U.V. radiation from each other. In contrast, the results obtained by the method of the invention, as shown in FIGS. 4, 5 and 6, distinguish clearly between the different samples.

The graph of FIG. 4 is a plot of S' against time at a fixed temperature, (100° C.) amplitude and frequency of oscillation (90° and 0.0625 Hz respectively). The results are directly comparable with those of FIG. 3, part of each sample of rubber having been used for the prior art test method and part for the method according to the invention. It will be seen from FIG. 4 that the value of S' increases with the duration of UV exposure. The indicated value of S' is seen to decrease slowly over the period of the test.

FIGS. 5 and 6 show the values 100° C. and 0.0625 Hz of S' and Tan Delta measured at a series of amplitudes on samples obtained by irradiating a different SBR 1502 from that used in the previous tests. The exposure times ranged from 0 to 3 hours. It can be seen that S' increases and Tan delta decreases with exposure. On the graph of S', discrimination between the various samples is adequate at an angle of 30°, but better at larger angles. When Tan delta measurements are used for distinguishing the samples, a preferred minimum angle of oscillation would be about 40°.

Figure 7A:
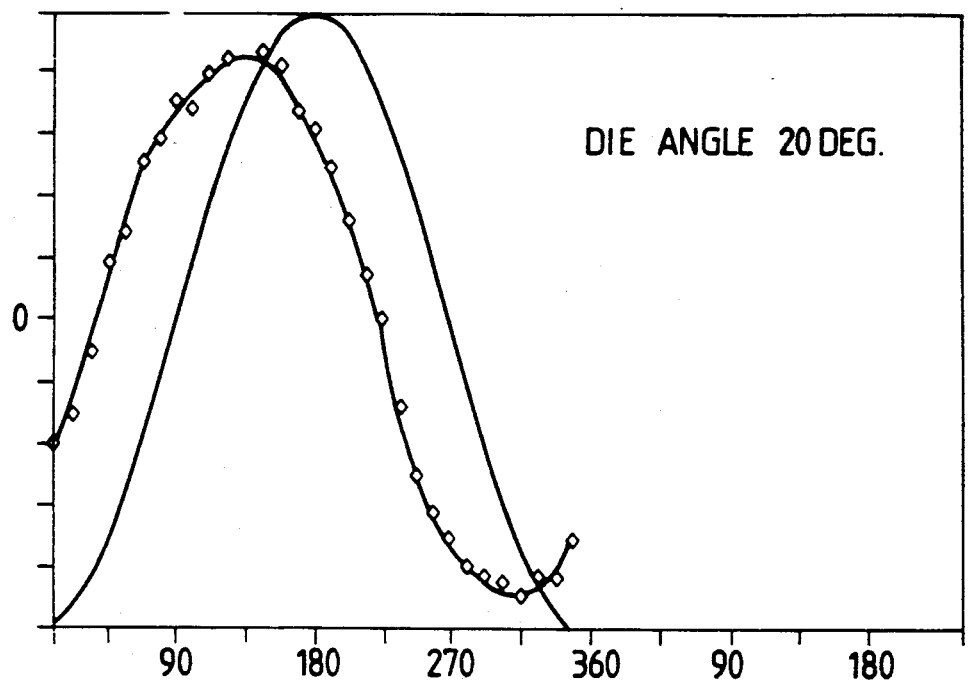
Figure 7B:
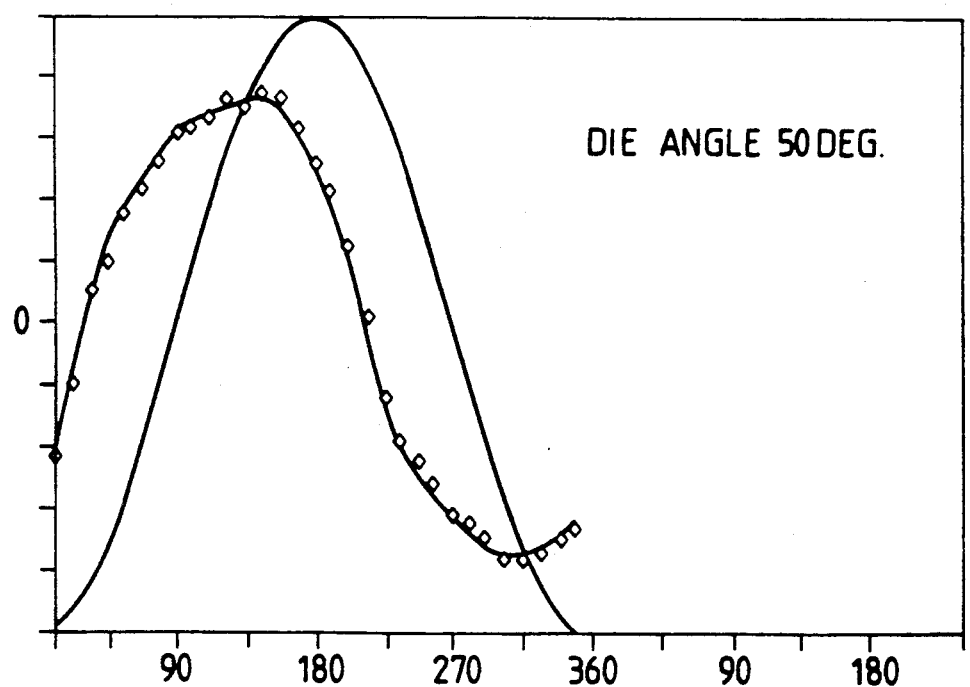
Figure 8A:
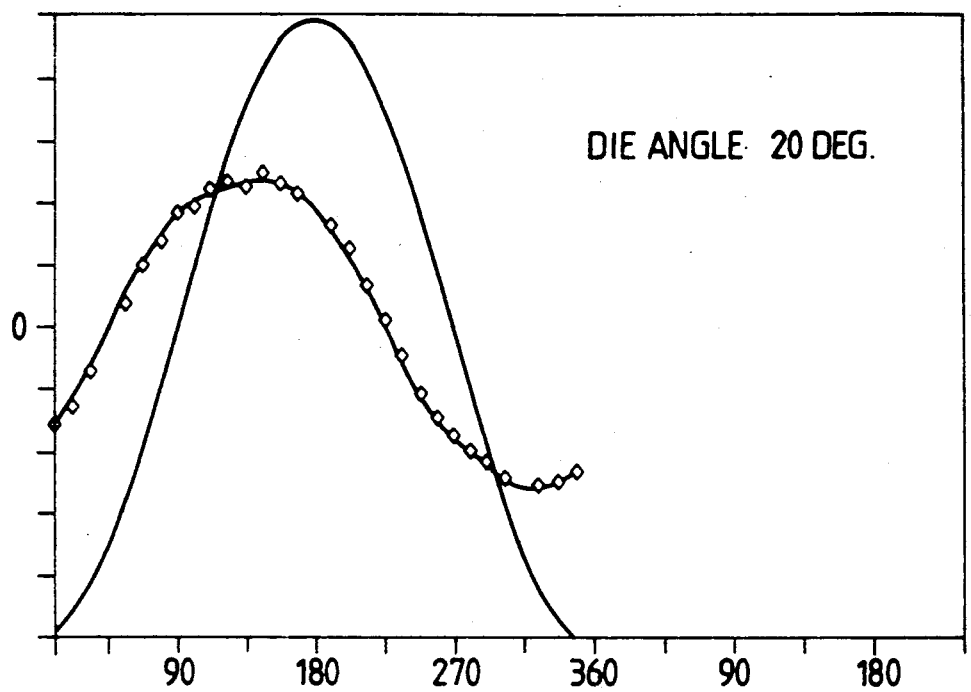
Figure 8B:
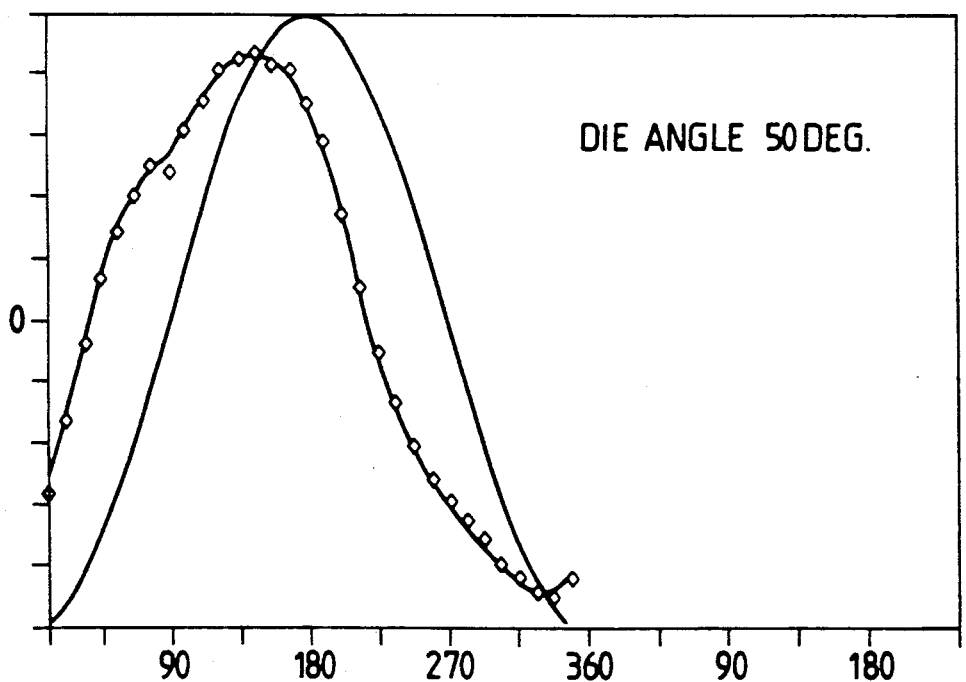

FIG. 7(a) and (b) and FIG. 8(a) and (b) show how the shape of the curve of relative torque calculated from harmonic analysis plotted against phase angle varies with the amplitude of oscillation. The sinusoidal motion of the lower die which applies shearing force is indicated by the continuous lines. In FIGS. 7(a) and 8(a), the amplitude of oscillation is 20°; in FIGS. 7(b) and 8(b) the amplitude of oscillation is 50°. The data of FIG. 7(a) and (b) were derived from measurements at 100° C. and 0.0625 Hz on ex-factory SBR-1502. Those of FIG. 8(a) and (b) were derived from measurements at 100° C. and 0.0625 Hz on SBR-1502 which has been subjected to U.V. radiation for 4.5 hours.

We claim:

1. A method of testing a sample of viscoelastic material held under pressure between two opposing, temperature-controlled dies, which comprises subjecting the sample to an oscillatory, rotary shearing force having a predetermined amplitude and frequency, and measuring a torque which is indicative of the response of the sample to the shearing force, characterised in that at least one measurement of said torque is made when the said predetermined amplitude is at least ±10° but not greater than ±360°, and said frequency is within the range 0.001 to 2 Hz.

2. A method according to claim 1 in which the oscillatory, rotary shearing force is applied by oscillatory rotation of one of the dies relative to the other, and the torque which is measured is the reaction torque of the other die.

3. A method according to claim 1 in which the said at least one measurement of torque is made at a predetermined amplitude in the range of ±10° to ±200°.

4. A method according to claim 3 in which the amplitude range is from ±20° to ±120°.

5. A method according to claim 4 in which the said at least one measurement of torque is made at a single amplitude.

6. A method according to claim 3 in which torque is measured at a series of different amplitudes which includes at least two within the range ±10° to ±120°.

7. A method according to claim 1 in which measurements of torque are made at two or more different frequencies of oscillation.

8. A method according to claim 1 in which the oscillatory shearing force is applied by sinusoidal motion.

9. A method according to claim 8 in which the torque measurements are subjected to harmonic analysis to produce a characteristic torque curve for the viscoelastic material.

10. A method according to claim 1 in which the oscillatory shearing force is applied by constant speed oscillatory motion, and torque measurement data are processed to provide output information corresponding to that obtainable from a standard Mooney shearing-disk viscometer.

11. Apparatus for testing a sample of viscoelastic material comprising two opposing dies movable between an open position and a closed position, and adapted, when in the closed position, to hold between them a sample of viscoelastic material under pressure, means for controlling the temperature of the dies, means for applying to the sample of viscoelastic material an oscillatory, rotary shearing force and means for measuring a torque which is indicative of the response of the sample to the shearing force, characterised in that the means for applying the shearing force comprise means for applying the shearing force at at least one amplitude of oscillation within the range ±10° to 360° and a frequency of oscillation within the range 0.001 to 2 Hz.

12. Apparatus according to claim 11 in which the means for applying the oscillatory, rotary shearing force comprise means for rotating one of the dies relative to the other, and the means for measuring the torque indicative of the response of the sample to the shearing force comprise means for measuring the reaction torque on the said other die.

13. Apparatus according to claim 12, comprising means for applying the shearing force at at least one amplitude of oscillation within the range ±10° to ±200°.

* * * * *